United States Patent [19]
Griebel

[11] Patent Number: 5,275,159
[45] Date of Patent: Jan. 4, 1994

[54] METHOD AND APPARATUS FOR DIAGNOSIS OF SLEEP DISORDERS

[75] Inventor: Peter Griebel, Freiburg, Fed. Rep. of Germany

[73] Assignee: Madaus Schwarzer Medizintechnik GmbH & Co. KG, Munich, Fed. Rep. of Germany

[21] Appl. No.: 854,241

[22] Filed: Mar. 20, 1992

[30] Foreign Application Priority Data

Mar. 22, 1991 [DE] Fed. Rep. of Germany ....... 4109529
Nov. 26, 1991 [DE] Fed. Rep. of Germany ....... 4138702

[51] Int. Cl.⁵ .................................................. A61B 5/00
[52] U.S. Cl. ..................................... 128/633; 128/670; 128/671; 128/716
[58] Field of Search ............... 128/670, 671, 630, 633, 128/706, 709, 710, 716, 666

[56] References Cited

U.S. PATENT DOCUMENTS

| | | | |
|---|---|---|---|
| 4,777,962 | 10/1988 | Watson et al. | 128/721 |
| 4,802,485 | 2/1989 | Bowers et al. | 128/633 |
| 4,834,532 | 5/1989 | Yount | 128/633 |
| 4,982,738 | 1/1991 | Griebel | 128/670 |
| 5,123,425 | 6/1992 | Shannon, Jr. et al. | 128/733 |

*Primary Examiner*—Kyle L. Howell
*Assistant Examiner*—Robert L. Nasser, II
*Attorney, Agent, or Firm*—Felfe & Lynch

[57] ABSTRACT

The physiological parameters of heart rate, respiratory and snoring sounds, the degree of oxygen saturation of the blood, and the bodily position of the patient are measured and stored in coded form by means of portable apparatus. The stored data are transferred to a computer and then analyzed. The mobile apparatus comprises a detection and storage unit (2) and the following pickups: three EKG electrodes (3), one laryngeal microphone (4), an oximeter-finger sensor (5) and a position pickup (6). The apparatus permits an ambulatory diagnosis of sleep apnea which is comparable in its meaningfulness to diagnoses based on stationary sleep laboratory tests for sleep apnea.

21 Claims, 4 Drawing Sheets

FIG. 1
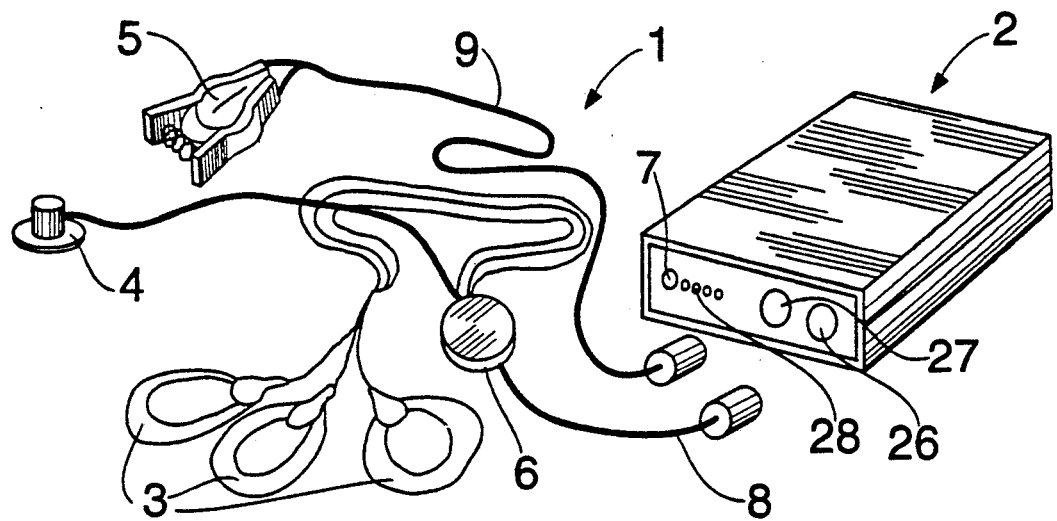
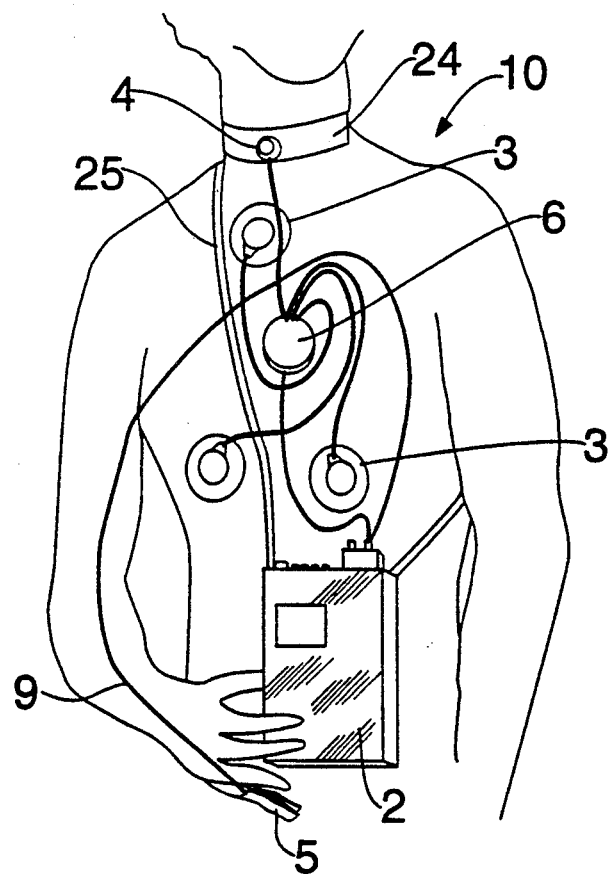
FIG. 2

METHOD AND APPARATUS FOR DIAGNOSIS OF SLEEP DISORDERS

BACKGROUND OF THE INVENTION

The invention relates to a method for the ambulatory detection and diagnosis of the sleep apnea syndrome, in which the physiological parameters of heart rate, loud breathing sounds and snoring sounds of the patient are detected and corresponding signals are generated. Sets of these that are detected in brief time intervals are stored in coded form in a portable apparatus, transferred to a computer, and analyzed by the latter, and especially variations of the individual signals in time and correlations between the various parameters are taken into account. The invention furthermore relates to an apparatus necessary for the practice of this method.

The symptom of sleep apnea is characterized by the combination of a respiratory failure, a considerable hypoxemia (i.e., a reduction of the oxygen content in the arterial blood) and heart rhythm disturbances. After an episode of apnea, a severe gasping for air and often also a terrifying awakening occur as a rule (see, for example, M. J. Tobin, M. A. Cohn, M. A. Sackner: Breathing abnormalities during sleep, Arch. Intern. Med. 1983; No. 143, pp 1221 to 1228).

The epidemiological significance of sleep apnea is increasingly being recognized; it is known that long and frequent phases of apnea in sleep often accompany cardiovascular and cardiopulmonary diseases as well as extensive psychophysical changes. Effects of sleep apnea are an excessively increased tendency to fall asleep during the day (in this case sleep apnea is statistically identified as the most frequent cause) and the occurrence of difficulty in falling asleep and sleeping through the night (in this case sleep apnea is described as the fifth most frequent cause (R. M. Coleman, H. P. Roffwarg, S. J. Kennedy: Sleep-wake disorders based on polysomnographic diagnosis. A national cooperative study. JAMA 1982; No. 247, pp. 997 to 1003)).

For some time the study of sleep-wake disorders has been performed in sleep laboratories in special clinics, in which a diagnosis can be performed by polysomnographic evaluation during sleep. These studies are time-consuming and costly; on account of the many parameters that have to be recorded they can be performed only by confining the patient. In addition to the high costs, such confinement has the disadvantage that the patient's sleep is disturbed by strange surroundings, which diminishes the value of such studies. Consequently there have been a number of efforts to eliminate the disadvantages of diagnosis with confinement and to cope with the large number of patients caused by the high prevalence.

One possibility is to recognize and diagnose sleep apnea syndrome in an ambulatory manner with the aid of portable detection and recording apparatus, avoiding confinement in sleep laboratories.

U.S. Pat. No. 4,982,738 describes a method and an apparatus (NLMS-non-laboratory monitoring system) for the ambulatory detection and diagnosis of the sleep apnea syndrome corresponding to the kind referred to above. In this method heart potentials (EKG) are measured relative to a third electrode with two electrodes to be applied to the upper body of a patient and fed to a peak level detector. The heart rate is determined by the time intervals between the peak values. The breathing and snoring sounds are picked up by an electret microphone to be applied to the patient's larynx and fed to two different threshold detectors, one threshold detector being sensitive over the entire frequency range (about 100 Hz to 15 Khz) and the other being sensitive only in the lower frequency range (about 100 Hz to 800 Hz typical for snoring) on account of the damping of the high frequencies of the signals with a filter. The threshold detectors respond when the applied signal exceeds the preset thresholds. The thresholds are adjusted so that loud breathing sounds are detected by the first-named threshold detector, and snoring is detected with the second detector. These physiological parameters, namely heart rate and presence or absence of breathing and snoring are measured together at time intervals of one second, and stored in binary code for each time interval in a RAM situated in the apparatus. The data stored during a period of sleep are transferred from the mobile apparatus to a computer and analyzed on the computer for a sleep apnea syndrome. Information as to the presence of an apnea can be derived from the changes in time of the heart rate and the breathing and snoring sounds and the correlations between these parameters. The seriousness of an apnea depends on the frequency of its occurrences, their severity and their duration. The method using the described apparatus has the disadvantage that it permits only detection of occurrence and duration, which leads to high sensitivity but not sufficient specificity of diagnosis. Information on the body position of the patient, which is important to the diagnosis, say, to distinguish between walking and laying down or dependence of obstruction on position in bed was not available. In the case of disease conditions, such as polyneuropathy, arteriosclerosis or diabetes, the heart rate does not change greatly as it does in apnea attacks, but remains virtually constant. In the presence of such conditions apnea is difficult to diagnose, because differential diagnosis using oxygen saturation for detection of apneas was not possible. In many cases, therefore, when the apparatus of the state of the art is used, it must be followed by confinement in a sleep laboratory.

SUMMARY OF THE INVENTION

A method for the ambulatory detection and diagnosis of the sleep apnea syndrome, which offers such great reliability of diagnosis that subsequent confinement in a sleep laboratory for observation will as a rule be unnecessary. In addition to determining the frequency the method also permits a quantitative determination of the severity and duration of apnea episodes and covers the body position and movements of the patient. A diagnosis of apnea is also possible in the case of the disease conditions mentioned above; vice versa, if their presence is unknown, indications of these conditions is provided. This includes the design of an appropriate apparatus.

In synchronism with the other parameters determined and recorded, the oxygen saturation of the blood and the bodily position of the patient are determined and stored in coded form by the portable apparatus, the stored sets of these parameters together with those of the other parameters are transferred to a computer and analyzed with the latter, so that a measure of the severity of individual episodes of apnea is obtained in the analysis on the basis of the duration and severity of periods of oxygen desaturation, and on the basis of changes in the bodily position a measure of the sleep disturbance caused by apnea is derived.

By means of the relationship between the simultaneous occurrence of intermittent snoring, cyclical variation of heart rate, and oxygen desaturation it is possible by analysis to distinguish between obstructive apnea, central apnea and some other sleep disturbances, such as myoclonus. In obstructive apnea the episodes occur more frequently in the supine position. Generally an apnea episode leads to a great change in the heart rate and to oxygen desaturation of the blood. If, however, desaturation is observed at a virtually constant heart rate, this can be considered an indication of a polyneuropathy, arteriosclerosis, diabetes or a threatened coronary infarction. To improve the quality of the diagnosis, it is advantageous to identify special events which if undetected might interfere in the analysis, such as getting in bed, waking up, or standing up and to quantify the time in bed. This can be accomplished, in addition to the continuous recording of the body position, by enabling the patient, in such an event, to press a button on the mobile apparatus. By measuring the time frame of the oxygen desaturation of the blood it is possible to determine the duration and severity of an episode of apnea.

The apparatus for the practice of the method described is a portable apparatus which contains means for detecting the heart rate, the breathing and snoring sounds, the degree of oxygen saturation of the blood and the bodily position of the patient, at brief intervals of time. Moreover, the apparatus has means for the recording of a number of sets of these parameters in coded form. The apparatus can also have means for the marking of certain detection time intervals, this being preferably a pushbutton switch. The testing time intervals can be of various length according to the different factors to be detected and registered; intervals of 1 to 10 seconds are preferred. In the case of another preferred embodiment, shorter intervals of as little as 0.1 sec can be used. In another embodiment, the length of the detection time intervals is variable, and the length can be set automatically as needed by the mobile apparatus. Especially short time intervals are then selected by the apparatus when an especially noteworthy event occurs, i.e., a possible episode of apnea.

The means for measuring the oxygen saturation of the blood include at least one light source and at least one light receiver, which are fastened to an extremity of the patient and serve for measuring the light absorption or reflection produced by the extremity. The light source or sources can be a light-emitting diode or diodes and the receiver or receivers can be a phototransistor or phototransistors. The wavelength of the light is preferably selected such that the change in the blood color associated with a change in the oxygen content of the blood can best be detected; this is the case in the red-light range. If light of two different wavelengths is used, the second light radiation used is preferably selected so that its reflectivity or transmissivity are as independent as possible of the oxygen content of the blood; this is the case in the infrared light range. The light of the second wavelength serves to obtain a reference level independent of the oxygen content by which the transmitted or reflected light that is sensitive to the oxygen content can be standardized. If the measurement of the color change is based on absorption, the light source or sources and light receiver or receivers are preferably disposed opposite one another on a mounting, with the light emitting and light receiving sides of the light source or sources and light receiver or receivers, respectively, facing each other. In a preferred embodiment, the mounting is a clip, the light source or sources and light receiver or receivers being disposed on confronting legs of the clip. In another preferred embodiment the mounting is a flexible strip which is bent into a U-shape at one end, the light source or sources and light receiver or receivers being fastened to the limbs of the U. In both embodiments the mounting is fastened to the patient's extremity so that body tissue is situated between the light source or sources and light receiver or receivers.

The means for detecting the patient's position contain preferably a hollow body to be fastened to the patient's upper body, with a ball of electrically conductive material inside it. The hollow body is advantageously a hollow tetrahedron at whose corners are electrical contacts which can be closed by the ball. The hollow tetrahedron can, for example, be so oriented that, in the supine position, lying on the left and right side, and in the upright position, the ball will come to rest in one of the corners, where it closes the contact. In the prone position the ball lies on a surface of the tetrahedron and makes no contact.

Advantageously, the means for the analysis of respiratory sounds are arranged such that they detect only the heavy snoring sounds produced by gasping for air after an episode of apnea. This can be accomplished by raising the threshold of the detector that is sensitive over the entire frequency range.

The devices provided for the detection of the patient's heart rate, breathing and snoring sounds, degree of oxygen saturation of the blood and bodily position are fastened to the patient's body and preferably connected to the portable apparatus by signal wires. In another preferred embodiment the signals from these devices are transmitted to the portable apparatus wirelessly, e.g., by electromagnetic waves. In this case there is no need to fasten the apparatus directly to the patient's body. Instead of a pushbutton on the apparatus for marking special events, a likewise wireless remote-controlled switching device can be used.

As the above statements indicate, the invention has the advantage that by measuring the degree of oxygen saturation it is possible to determine the severity of the apnea attacks and thus achieve a quantitatively accurate analysis of the sleep apnea syndrome. The different occurrence of events in snoring, heart rate, oxygen saturation and body positions permit a determination of restlessness in sleep and a diagnostic distinction between apnea, hypopnea, myoclonus and other sleep disorders. Furthermore, episodes of apnea can be diagnosed also in the presence of disorders in which the heart rate remains virtually constant; the discovery of such disorders is also possible. In general, therefore, in comparison with the state of the art, the invention offers substantially better and broader possibilities for the diagnosis of the sleep apnea syndrome. It has been found that data obtained by means of the method of the invention, using the apparatus of the invention, are so very meaningful that, in the case of the great majority of patients no further testing was necessary after the data were evaluated by technically trained personnel. In spite of their simplicity, diagnoses can be made with the apparatus according to the invention which are comparable in reliability with those of long-term tests with confinement in sleep laboratories, without the falsifying influences involved in a stay in a sleep laboratory.

BRIEF DESCRIPTION OF THE DRAWINGS

FIG. 1 is a perspective view of a portable detection and recording apparatus,

FIG. 2 a perspective view of the apparatus in working position on a patient's body, FIG. 3 a side view of an oximeter sensor with a stiff finger clamp for detecting the oxygen saturation level by measuring light absorption.

DETAILED DESCRIPTION OF THE PREFERRED EMBODIMENT

Figure 3:
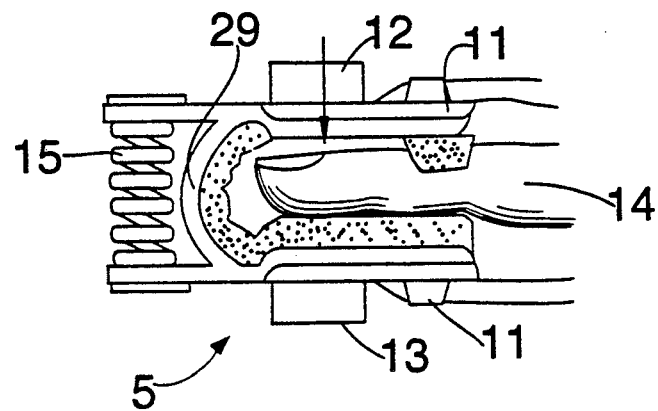

The detection and recording apparatus 1 in FIG. 1 consists of the actual detection and recording unit 2 with a pushbutton switch 7 on the front and the following different pickups: three EKG electrodes 3, a laryngeal microphone 4, an oximeter finger sensor 5, a position detector 6 and two connecting cables 8 and 9 each with a plug.

In FIG. 2 is shown how the pickups are positioned on the body of a patient 10.

The EKG electrodes 3 are commercial disposable electrodes which are fastened to the upper body of the patient 10; two of them measure the heart potential relative to the third electrode. The laryngeal microphone 4 is an electret microphone which is fastened with a strap 24 to the neck of the patient 10 so that it lies against the larynx. The side of the microphone 4 that is in contact with the larynx of the patient 10 is provided with an annular isolating pad and an annular self-adhering disposable bandage.

In FIG. 3 is shown an embodiment of a finger sensor 5. It comprises two stiff clip legs 11 joined together by a flexible bow 29. A compression spring 5 is disposed on one side of the bow 29 between the legs 11 and presses together the legs 11 on the other side of the bow to grip a finger 14 of the patient 10. On the upper leg 11 are two light emitting diodes 12, and on the lower one, two phototransistors 13. Part of the light emitted by the light emitting diodes 12 passes through the finger 14 and is received by the phototransistors 13, and another part is absorbed by the tissue of the finger. This absorption measurement is performed at wavelengths of 660 nm and 925 nm. The absorption of the light of the first wavelength depends very greatly on the oxygen content of the blood; the absorption of the light of the second wavelength is virtually independent of it.

Figure 4:
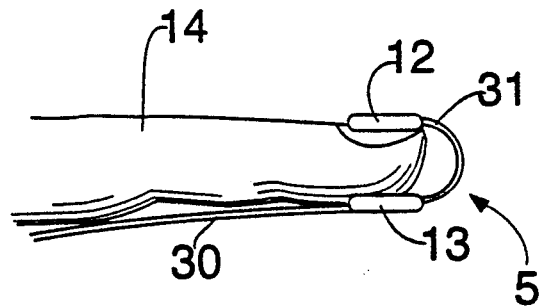
FIG. 4 is a side view of another embodiment of an oximeter sensor corresponding to FIG. 3, but with a flexible strip instead of a stiff clip.

Another embodiment of a finger sensor 5 is shown in FIG. 4. It comprises a flexible strip 30 which is bent to a U-shape at one end. At the end of the free limb 31 of the U there are two light emitting diodes 12. On the other limb are two phototransistors 13 opposite one another. The U-shaped strip 30 is pushed over the tip of finger 14. The finger sensor is held in place by means of one or more straps with hook-and-loop fasteners or disposable adhesive tapes. As regards the light used and its absorption characteristics, this embodiment is the same as the embodiment in FIG. 3.

Both of the described embodiments of the finger sensor 5 can be installed easily and in the correct position by medical technical assistants. The embodiment in FIG. 3 permits an especially easy and quick placement, while the embodiment in FIG. 4 offers an especially secure fixation and, since it exerts no pressure on the finger, provides good wearing comfort.

The position pickup is fastened to the upper body of the patient 10 with an adhesive ring in a specific orientation indicated by positioning instructions printed on its exterior. The position pickup 6 comprises a hollow tetrahedron containing a ball of electrically conducting material, and in its corners electrical contacts are disposed which can be closed by the ball. The hollow tetrahedron is oriented so that, in the supine position, or lying on the left side or the right side, or in the upright position, the ball will come to rest in one of the corners, where it closes the contact. In the prone position the ball remains on a surface of the tetrahedron and makes no contact. The leads running from the microphone, the EKG electrodes 3 and the position pickup 6 are combined in a single cable 8 which can be attached by a 15-pin plug to the apparatus 2. The finger sensor 5 has its own cable 9 to connect it to the apparatus 2 with a 9-pin plug.

The analyzing and recording unit 2 has such small dimensions (190×135×45 mm) and such light weight (about 700 g) that it can be carried invisibly on the body by a shoulder belt 25 under the clothing. The unit 2 has on its front side two multi-pin receptacles 26 and 27, respectively, into which the corresponding plugs of the connecting cables 8 and 9 can be pushed and secured. Beside the push-button switch 7, there are also four light emitting diodes 28 on the unit to check the operation of the unit 2 after it has been put on. To carry the stored data to a computer, a data transfer cable, not shown, is provided. Power is supplied either by six small 1.5-volt batteries or by corresponding rechargeable batteries.

Figure 5:
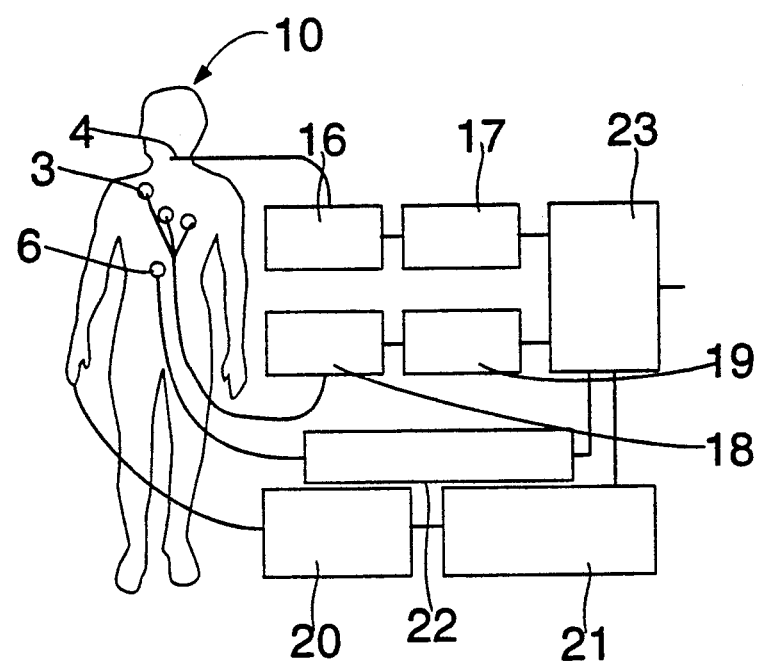
FIG. 5 is a block circuit diagram of the detection and recording apparatus.

The wiring diagram in FIG. 5 shows the signal processing in the analyzing and storage unit 2. The signals picked up by the laryngeal microphone 4 are amplified by an amplifier 16 and distributed in two channels; the signals of one channel are then carried through a filter 17. The filter 17 damps signals above 800 Hz with a 12-decibel/octave damper. Not shown are the unfiltered branch and the threshold detectors provided for both channels. The threshold detector which is connected to the filter 17 and is sensitive in the frequency range from about 100 Hz to 800 Hz is set to a medium threshold level such that the signals or normal snoring sounds, but not smooth respiratory sounds, will exceed the threshold. The second threshold detector responding to the entire frequency range from about 100 Hz to 15 Khz is set to such a high threshold level that the threshold is generally exceeded only by the very loud snoring and gasping noises following an apnea attack. The information, "threshold exceeded" and "threshold not exceeded," constitutes a useful binary value for storage and further processing.

The signals originating from the phototransistors 13 of the finger sensor 5 are first amplified by a signal amplifier 20. Then in a desaturation analyzer 21 the oxygen saturation level of the blood is determined and binary-coded. The signal levels correspond to the intensities of the light wavelengths emitted by the photodiodes 12 and transmitted through the tissue of the finger 14. Since the absorption of the shorter wavelength light depends greatly on the oxygen content of the arterial blood, but the longer wavelength light is hardly affected at all by the oxygen content, a measure of the oxygen saturation of the blood can be derived from the signal level of the shorter wavelength light after standardization to the signal level of the longer wavelength light. An accuracy of up to 2% is achieved thereby.

The signals originating from the EKG electrodes 3 are first amplified by an EKG amplifier 18 and then are fed to a heart rate analyzer 19 which determines the heart rate. The determined value of the heart rate is then binary-coded.

The four possible position signals originating from the position pickup 6 are analyzed in a position analyzer 22 and also binary-coded. Not shown in FIG. 4 is the pushbutton switch 7.

All of the parameters are continually picked up in parallel, coded, and stored successively in sets of parameters that belong together in time in a RAM storage 23 with at least 128 kB storage capacity. The basic scanning interval amounts to 1 second; the oxygen saturation is read every 2 seconds, and the body position is read every 10 seconds, and renewed. The recording time amounts to at least 22 hours. The stored data for a recording period can be transferred via a modem not shown, with a transmission rate of 9200 baud, through an RS232 port of an XT or AT personal computer not shown. By using memory chips of greater capacity, a total storage capacity of several megabytes can also be achieved. In this way shorter scanning intervals or longer total recording times can be established.

When starting up at the beginning of a recording period, the attachment of the connecting cable 8 to the unit 2 automatically initiates a self-test. It lasts several minutes and is performed with the aid of the light emitting diodes 28. One of the diodes 28 is provided for checking the EKG function, the saturation measurement and the two respiratory sound channels. The light emitting diode associated with the EKG channel will light up upon the detection of an R wave and if operation is correct it blinks in synchronism with the R waves. The light emitting diode associated with the oxygen saturation channel lights during the first 30 seconds of the self-test if no valid value is present; this is the case, for example, if the finger sensor is not fastened to the finger in the correct position. If operation is correct this diode remains out. The two light emitting diodes associated with the respiratory sounds light up when the threshold is exceeded. If operation is correct these two diodes remain out in the normal state and can be made to light up by simulating snoring noises or very loud breathing noises. After the self-test the unit 2 begins the detection and storage of the above-mentioned physiological data for the duration of a data recording period.

Figure 6:
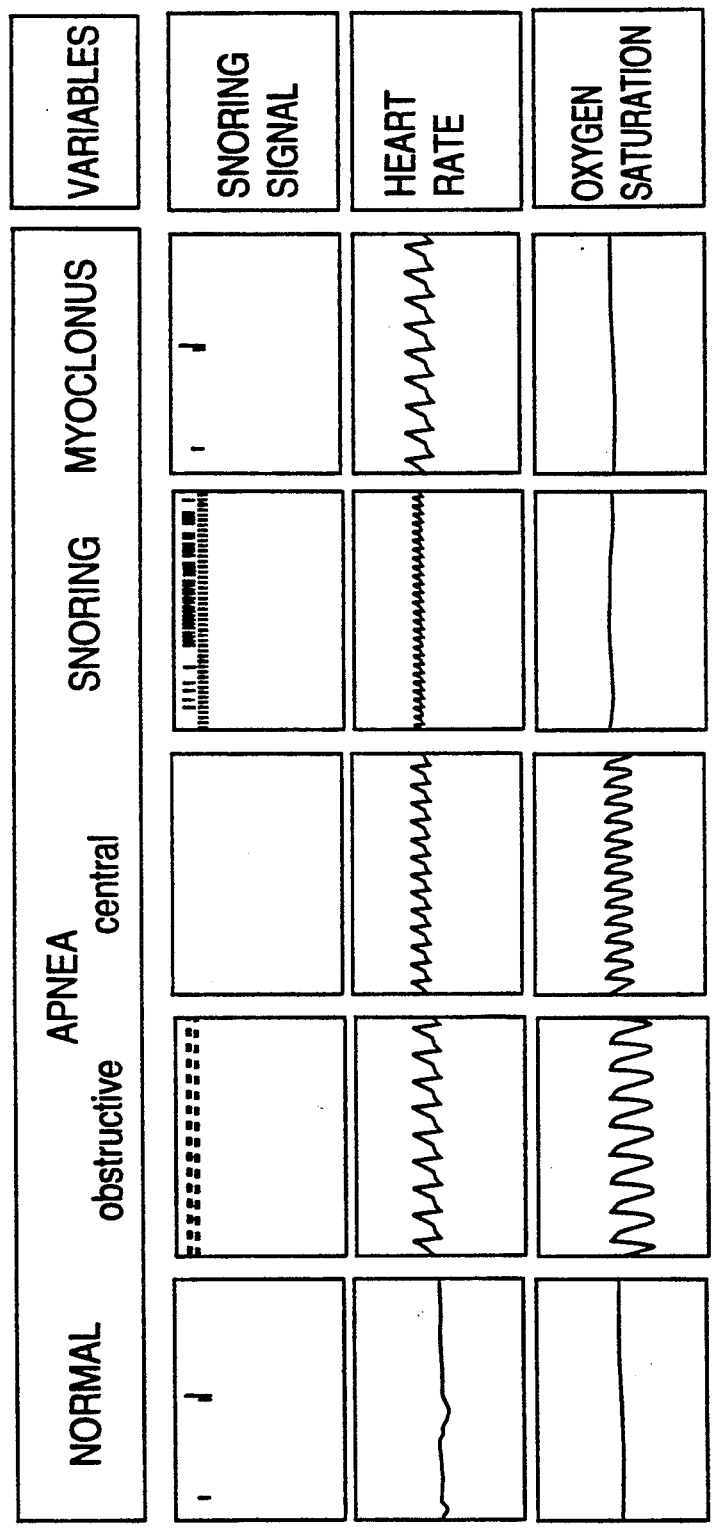
FIG. 6 is a graphic illustration of the correlation between monitored parameters and sleep disorders.

At the end of a data recording period the data stored in the mobile unit 2 can be transferred to a computer for evaluation. In the evaluation the data can be processed and displayed in three different ways:
i) The measured parameters (respiratory sounds, heart rate, oxygen saturation, body position) are represented together graphically as a function of time for the entire period of study. This graph shows quantitatively the common progress of these parameters in time and thus especially also the correlations among them in compressed form (e.g. 2 hrs/trace) or in full disclosure (e.g. 10 min/trace). It has the advantage of containing all of the recorded information; interpretation, however, requires a certain amount of time. FIG. 6 shows three of these parameters plotted for a ten minute interval.
ii) Some parameters are combined in time and represented in the form of histograms and tables. For example, a graphic representation of the distributions of the measured heart rates at successive 10-minute intervals, a graphic representation of the distribution of the measured oxygen saturation levels, and representation of the desaturation levels as a function of the duration and frequency of their occurrence, in the form of diagrams and tables. These representations no longer manifest the total development in time and all correlations between the measured parameters, but they do permit a faster interpretation.
iii) From the data the number of episodes in which apnea was probably involved is directly determined, and expressed as the episodes-per-hour units. Three such indexes are provided: the intermittent snoring index (ISI), the heart rate variation index (HVI) and the oxygen desaturation index (ODI). The simultaneous occurrence of at least 2 of those was validated to give an equivalence of the apnea index.

For the computation of the snoring index, pauses between snores, which last between 11 and 60 seconds, are counted over the entire examination period and divided by the number of hours in the examination period. Pauses of this length are typical of apnea episodes.

To determine the heart rate variation index, first a relative heart rate is computed by dividing the momentary heart rate by the running average of the heart rate of the previous 300 seconds. Relative heart rate frequencies between 90% and 109% are associated with the so-called 100% class; other frequencies are outside of this class. The heart rate variation index gives the number of events in the test period in which the relative heart frequency leaves the 100% class and returns to it within 11 to 60 seconds, divided by the number of hours in the test period. Thus, the heart rate variations are analyzed as they occur in synchronism with the apnea episode.

To determine the oxygen desaturation index, first the basal saturation level is determined by adding the highest oxygen saturation values from 2 to 10 preceding measurements, and the sum is divided by the number of measurements. A desaturation phase is present when the saturation level decreases by a preset percentage from the basal saturation level and lasts until a certain level of resaturation is reached again after the decrease. The oxygen desaturation index gives the number of desaturation phases in the test period divided by the number of hours in the test period. It detects the desaturation phases as they occur, also in synchronism with the apnea episode.

All three indexes directly give the number of significant changes which determine the events per hour. In case of obstructive sleep apnea the three indexes give approximately the same value. Great differences between the three indexes can indicate the presence of special disorders, as mentioned in the beginning. Overall, the determination of the three indexes provides an extremely quick and significant judgment of sleep disorder events.

FIG. 6 is a raw data display of the snoring, heart rate, and oxygen saturation signals as recorded during ten minute intervals and correlated to several sleep disorders diagnosed according to the invention. These graphs are the representation of the recorded raw data and easily plotted from the collected data and provide a high resolution for a quick check by the physician against the different indexes. They also provide a readily understood basis for the various diagnoses.

Note that the snoring signal appears as a lower trace, which represents a low intensity signal, and an upper trace, which represents a sound level exceeding a certain threshold. Changes in body position are also plotted, but have been deleted here for simplicity. A plot over a two hour period is usually also examined by the physician and is useful for getting the overall picture identifying periods where closer scrutiny is desired.

In a normal subject, the three variables plotted present a homogenous picture. No repetitive oxygen desaturations or changes in heart rate occur, and snoring does not occur. Arousals would be apparent from sudden increases in heart rate and changes in body position (not shown).

In a patient with obstructive sleep apnea (OSA) the three plotted variables follow a cyclical pattern. All three events always occur in connection with OSA. During periods when no respiratory sounds are detected, the heart rate falls and oxygen desaturation occurs. Resumption of breathing is marked by explosive snoring, together with an increase in heart rate and oxygen resaturation.

The blank intervals between snoring clusters represent the apneic interval. In some cases, though, the snoring clusters that appear at the resumption of breathing may not be separated by completely blank spaces, but by a pattern of regularly spaced black snoring dots. This pattern represents obstructive hypoapnea with a significant degree of upper airway narrowing, and is not to be confused with continuous snoring.

In a patient with central apnea there is typically no snoring, and body position will not be relevant. Heart rate and oxygen saturation are synchronous but less pronounced.

Continuous snoring is marked by continuous snoring signals with little or no oxygen desaturation and irregular variations in heart rate, which indicates upper airway resistance syndrome (UARS) which should be subject to therapy if daytime somnolence is a problem.

In nocturnal myoclonus with arousals, the cyclical changes are restricted to the behavior of the heart rate. Snoring and oxygen saturation show a normal evolution, independent of heart rate. If myoclonus is combined with OSA, the cyclical snoring and oxygen desaturations will be present. However, the slope of the increase in heart rate is steeper in myoclonus than in OSA.

Insomnia is indicated by an enormous number of body position changes, a lot of irregular heart rate variations, and a lot of irregular sound appearances. Oxygen desaturations do not occur.

Diagnoses with the inventive system are still possible when other conditions are present. For example, patients with autonomic nervous system dysfunction exhibit very little change in heart rate, even when they are physically active. The same is also true for subjects with cardiac pacemakers. However, patients with OSA will still exhibit the repetitive oxygen desaturations and intermittent snoring.

The foregoing is exemplary and not intended to limit the scope of the claims which follow.

I claim:

1. Method for the ambulatory detection and diagnosis of sleep disorders in a patient, comprising
   sensing heart potentials and generating a heart rate signal,
   sensing respiratory sounds and generating loud breathing signal and a snoring signal from said respiratory sounds,
   sensing degree of oxygen saturation in the patient's blood and generating an oxygen saturation signal,
   storing said heart rate signal, loud breathing signal, snoring signal, and oxygen saturation signal over time as stored signals, and
   comparing said stored signals to determine whether each one of obstructive sleep apnea, central apnea, continuous snoring, upper airway resistance syndrome, and nocturnal myoclonus is present.

2. Method as in claim 1 wherein obstructive sleep apnea is diagnosed by regular, synchronous variations in heart rate, snoring, and oxygen saturation.

3. Method as in claim 1 further comprising diagnosing the severity of both obstructive sleep apnea and central apnea form the duration of periods of oxygen desaturation and the amount of oxygen desaturation in said periods.

4. Method as in claim 1 further comprising
   sensing body position and generating a body position signal, and
   storing said body position signal over time as one of said stored signals.

5. Method as in claim 4 wherein obstructive sleep apnea is diagnosed by regular, synchronous variations in heart rate, snoring, oxygen saturation, and body position.

6. Method as in claim 4 wherein said body position signal is compared to said other stored signals and a measure of unrest during sleep is also determined.

7. Method as in claim 1 wherein central apnea is diagnosed by regular, synchronous variations in heart rate and oxygen desaturation.

8. Method as in claim 1 wherein one of continuous snoring and upper airway resistance syndrome is diagnosed by a substantially continuous pattern of snoring signals without significant changes in oxygen saturation and with only irregular variations in heart rate.

9. Method as in claim 1 wherein said stored signals are further compared to indicate whether a further disorder consisting of one of polyneuropathy, arteriosclerosis, diabetes, and a threatened coronary infarction is present, said further disorder being indicated when oxygen desaturation is detected at a substantially constant heart rate.

10. Method as in claim 1 wherein the patient performs the additional step of marking time intervals with special events comprising lights out and waking up, which special events are stored over time as stored signals.

11. Method as in claim 1 wherein said loud breathing signal is generated for respiratory sounds having a first frequency range and generates said snoring signal for a second frequency range which is a lower part of said first frequency range.

12. Apparatus for the ambulatory detection of physiological factors in a patient for use in diagnosing sleep disorders, comprising
    means for sensing heart potentials and generating heat rate signals,
    means for sensing respiratory sounds and generating a loud breathing signal and a snoring signal,
    means for sensing degree of oxygen saturation in the patient's blood and generating an oxygen saturation signal, means for storing said heart rate signal, loud breathing signal, snoring signal, and oxygen saturation signal over time, and means for comparing said stored signals to determine whether each one of obstructive sleep apnea, central apnea, continuous snoring, upper airway resistance syndrome, and nocturnal myoclonus is present.

13. Mobile apparatus as in claim 12 wherein said means for sensing degree of oxygen saturation comprises a light source and a light receiver for attachment to an extremity of the patient in facing relationship, said receiver generating a signal representing at least one of light absorption and reflection in said extremity.

14. Mobile apparatus as in claim 13 further comprising a U-shaped clip to which said light source and light receiver are fixed.

15. Mobile apparatus as in claim 12 further comprising means for detecting body position and generating a body position signal, said means for storing further storing said body position signal over time.

16. Mobile apparatus as in claim 15 wherein said means for detecting body position comprises a hollow member having electrical contacts therein and a conductive ball which bridges different contacts depending on the position of the patient.

17. Mobile apparatus as in claim 16 wherein said hollow member is a tetrahedron.

18. Mobile apparatus as in claim 12 wherein said means for sensing respiratory sounds generates said loud breathing signal for a first frequency range and generates said snoring signal for a second frequency range which is a lower part of said first frequency range.

19. Method for the ambulatory detection and diagnosis of sleep disorders in a patient, comprising sensing heart potentials and providing a heart rate signal, sensing respiratory signals and generating a loud breathing signal and a snoring signal, sensing degree of oxygen saturation in the patient's blood and generating an oxygen saturation signal, sensing the patient's body position and generating a body position signal, storing said heart rate signal, loud breathing signal, snoring signal, oxygen saturation signal, and body position signal, and comparing said stored signals to determine whether each one of obstructive apnea, central apnea and nocturnal myoclonus is present.

20. Method as in claim 19 wherein said stored signals are further compared to determine whether upper airway resistance syndrome is present.

21. Method as in claim 1 wherein the severity of both obstructive apnea and central apnea is determined from the duration and depth of periods of oxygen desaturation.

* * * * *